(12) United States Patent
Fitzgerald

(10) Patent No.: US 8,394,627 B2
(45) Date of Patent: Mar. 12, 2013

(54) HOME TEST KIT FOR DETECTING FECAL BLOOD

(75) Inventor: G. Joseph Fitzgerald, Largo, FL (US)

(73) Assignee: Life Fit Testing, LLC, Largo, FL (US)

( * ) Notice: Subject to any disclaimer, the term of this patent is extended or adjusted under 35 U.S.C. 154(b) by 0 days.

(21) Appl. No.: 12/900,714

(22) Filed: Oct. 8, 2010

(65) Prior Publication Data

US 2012/0028294 A1 Feb. 2, 2012

Related U.S. Application Data

(60) Provisional application No. 61/250,041, filed on Oct. 9, 2009.

(51) Int. Cl.
*C12M 3/00* (2006.01)

(52) U.S. Cl. ...................... 435/288.1; 435/810; 435/975

(58) Field of Classification Search ................ 435/8, 28, 435/810, 975, 288.1; 436/66
See application file for complete search history.

(56) References Cited

U.S. PATENT DOCUMENTS

| | | | |
|---|---|---|---|
| 4,365,970 A * | 12/1982 | Lawrence et al. | 436/66 |
| 4,492,124 A * | 1/1985 | Fleisher et al. | 73/864.44 |
| 4,862,899 A | 9/1989 | Bucaro | |
| 5,416,025 A | 5/1995 | Krepinsky et al. | |
| 6,759,204 B2 | 7/2004 | Benistant et al. | |
| 7,090,997 B2 | 8/2006 | Sasatsu et al. | |
| 7,592,181 B2 * | 9/2009 | Clawson | 436/66 |
| 2007/0037296 A1 * | 2/2007 | Goulden | 436/514 |
| 2008/0286831 A1 * | 11/2008 | Liang | 435/34 |

* cited by examiner

*Primary Examiner* — Ralph Gitomer
(74) *Attorney, Agent, or Firm* — Michael A. Myers; Shumaker, Loop & Kendrick, LLP

(57) ABSTRACT

A home test kit for detecting fecal blood includes a scoop device for collecting a fecal sample, a luminescent for mixing with the sample, a hollow container for containing the sample, water and the luminescent, or luminol during use of the kit. A base may be provided for supporting the container during testing, and the container may include an integrally formed lid. Detection of the blood in the sample is possible because the luminescent undergoes a light-producing reaction that involves, as a reactant or catalyst, blood or blood components or products. The blood is thus visible, or glows in darkened surroundings. The kit is compact, easy to use, and formed from biodegradable material for easy disposal.

8 Claims, 1 Drawing Sheet

HOME TEST KIT FOR DETECTING FECAL BLOOD

CROSS REFERENCE TO RELATED APPLICATIONS

This application claims the benefit of U.S. Provisional Application No. 61/250,041, filed Oct. 9, 2009, the disclosure of which is hereby incorporated by reference.

FIELD OF THE INVENTION

The present invention relates generally to the field of health care and home test kits, and more particularly, to a home test kit for detecting fecal blood.

BACKGROUND

Colorectal cancer screening is highly effective in reducing mortality. Only sixty percent of adults, however, are up to date with tests recommended by current guidelines. Researchers and clinicians are therefore eager to find ways to improve screening rates. One method, known as a fecal occult blood test (FOBT) finds blood in the stool by placing a small sample of stool on a chemically treated card, pad or cloth wipe. A special chemical solution is then put on top of the sample.

If the card, pad or cloth, turns blue, there is blood in the stool sample. A FOBT may be done to check for some intestinal conditions or colorectal cancer. Blood in the stool may be the only symptom of colorectal cancer, but not all blood in the stool is caused by cancer. Other conditions that can cause blood in the stool include hemorrhoids, anal fissures, peptic ulcers, ulcerative colitis, certain gastroesophageal reflux diseases or use of nonsteroidal anti-inflammatory drugs (NSAIDs), such as aspirin or the like.

Before the invention of applicant's home test kit, the following shortcomings of FOBTs prevented many of the previously mentioned conditions from being discovered: messiness of testing; clinicians' or other employee's failure to perform fecal occult blood testing—handling feces in any manner is not desirable to do; embarrassment; the escalation of the cost for tests; the length of time and inconvenience to conduct the test—present test procedures include sending the stool sample (in some cases via U.S. mail) to a location other than where it was placed on the card; and safe, clean environmentally conscious means for disposing of the test sample and components after completing the test were not available.

Thus, it would be advantageous to provide a new test kit for detecting fecal blood that could be performed in the privacy of one's home. It would be desirable that such a kit be compact, easy to use, and biodegradable. It would also be novel if such a kit would address the aforementioned shortcomings of prior fecal occult blood tests.

SUMMARY OF THE INVENTION

The invention provides a simple and convenient kit and method for detecting fecal blood in the privacy of one's home. One embodiment of the home test kit for detecting fecal blood includes a scoop device for collecting a fecal sample, luminol for mixing with the sample, and a hollow container with an open end and a closed end for containing a mixture comprising the sample, the luminol, and water. Upon performing the method of the invention, the mixture luminesces or glows as a result of iron present in hemoglobin such that blood in the sample is visually detectable by the human eye when the mixture is viewed in darkened surroundings.

In one aspect of the invention, the kit includes a compound which, when present in an aqueous solution with at least one of blood, blood fractions, blood components and hemoglobin, results in a chemiluminescence. In another aspect, the compound undergoes a reaction in aqueous solution that is catalyzed by at least one of blood, blood fractions, blood components and hemoglobin. In further aspects, the reaction is catalyzed by the hem iron of hemoglobin.

In another aspect, the kit may include a base with a cavity for receiving the closed end of the container so the container can be securely and releasably held in an upright attitude for viewing.

In still another aspect, the kit may include a lid for closing the open end of the container. The lid may be connected to or integrally formed with the container.

In yet another aspect of the invention, the container, the lid, and the base may be formed from a biodegradable material.

One object of the invention is to provide a clean and convenient method of detecting fecal blood in the privacy of one's home. Related objects and advantages of the invention will be apparent from the following description.

DETAILED DESCRIPTION OF INVENTION

The details of the invention, both as to its structure and operation, may be obtained by a review of one potential commercial embodiment. The disclosure of this potential commercial embodiment is not intended to be limiting with respect to the potential application of other aspects of the invention. The home test kit for detecting fecal blood is compact, easy to use, and biodegradable. The kit also solves the shortcomings of prior fecal occult blood tests. The test may be carried out from start to finish in the privacy of one's home and, therefore, could be used to test human or pet stool.

Figure 1:
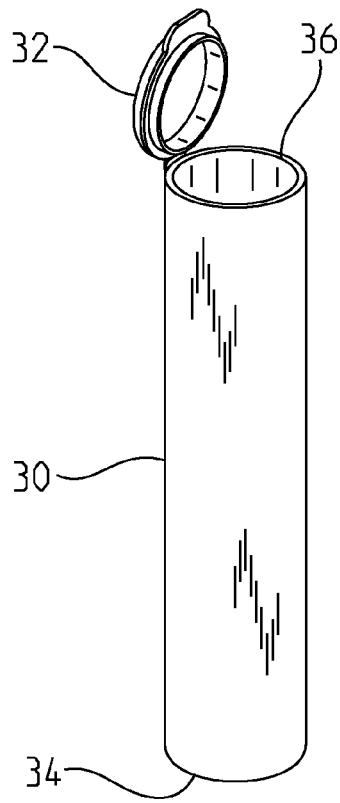
FIG. 1 is an isometric view of an embodiment of the container of the invention.
Figure 3:
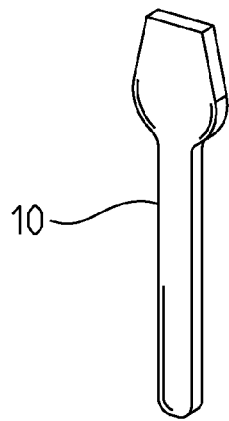
FIG. 3 is an isometric view of an embodiment of the scoop of the invention.
Figure 4A:
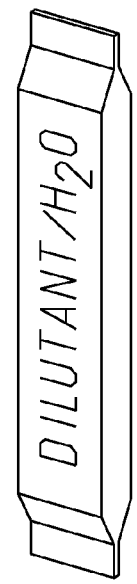
FIG. 4A is an isometric view of packaging for containing dilutant or water of the kit of the invention.

Generally, the kit includes a scoop device 10 characterized by a handle end and a scoop end for collecting a fecal sample (not shown). As shown in FIG. 3, the scoop device may be formed in a paddle or scoop shape such that it includes a handle end and an opposite scoop or sample collection end and sized such that it is easy to manipulate, but small enough for packaging, preferably 2 to 7 inches in length. The scoop device is formed from a substantially rigid material so that it may be easily manipulated and the sample easily collected.

In a preferred embodiment, the scoop device 10, including the other parts of the kit identified below, is biodegradable or, preferably, formed from a substance that may dissolve or disintegrate in water so that the scoop 10 and the entire kit may be flushed in the toilet after use. Samples of such material include, paper and other cellulosic materials, materials formed substantially from starch, gum, or alginate material such as agar and so on.

The kit includes a compound which, when present in an aqueous solution with at least one of blood, blood fractions, blood components and hemoglobin, results in a chemiluminescence. In further embodiments, the compound undergoes a reaction in aqueous solution which is catalyzed by at least one of blood, blood fractions, blood components and hemoglobin. In further embodiments, the reaction is catalyzed by the hem iron of hemoglobin.

The kit includes a luminescent, preferably dry luminol ($C_8H_7N_3O_2$) 20, which may be packaged and contained in a container 22. Some compounds related to luminol such as: Luminol, hemihydrate 3; Luminol, Na salt; Luminol, HCL; isoluminol; isoluminol, monohydrate; and isoluminol ABEI, to name some examples, may be more or less suitable for use with the method of the invention. Luminol may be synthesized using known means beginning from 3-nitrophthalic acid. First, hydrazine ($N_2H_4$) is heated with the 3-nitrophthalic acid in a high-boiling solvent such as triethylene glycol. Nitrophthalhydrazide is formed by a condensation reaction. Reduction of the nitro group on the Nitrophthalhydrazide yields luminol.

In an embodiment, the container 22 containing the luminol 20 is paper and includes a perforated portion 24. The container 22 may be formed of any suitable material having desirable mechanical physical properties so that it may be safely and properly disposed of.

Figure 2:
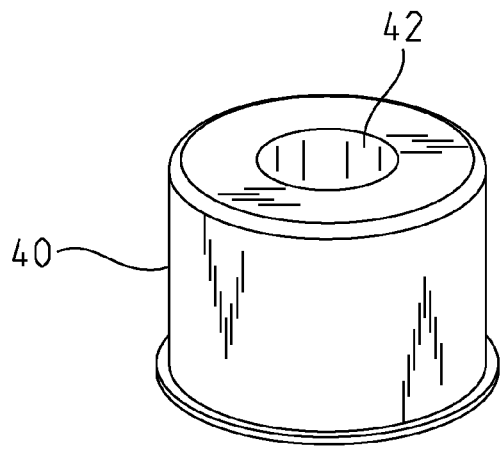
FIG. 2 is an isometric view of an embodiment of the container base of the invention.
Figure 4:
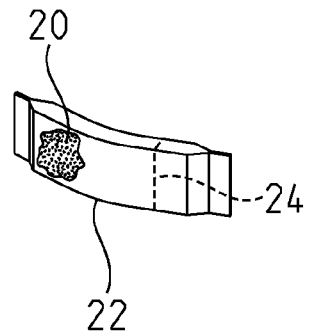
FIG. 4 is an isometric view of an embodiment of the package container of the invention partially cut away to show the luminol.

The kit also includes a hollow container 30 for containing the fecal sample and the luminol during use of the kit. The container is also preferably formed of a biodegradable (or water soluble substance, as described above) and may include lid 32, preferably formed integrally with or attached to the container 30. The container is preferably substantially transparent in order to see the luminescence described in detain below. Those skilled in the art will recognize that the container may be formed in any shape and size (with or without a lid, whether integral or not) so long as it's easy to use and convenient to dispose. The kit may include a base 40, shown in FIG. 2, with a cavity 42 for receiving the container. In this manner, the container may be securely and releasably supported in an upright position with its closed end 34 in the cavity to avoid spilling the sample during testing.

The kit may be packaged in a protective package like the one shown in FIGS. 5-6. The packaging of FIG. 5 includes a specially shaped recess for receiving the components of the kit and protecting them during shipment. The packaging may include a lid with an opening. The size of the opening is large enough to see at least a portion of the components of the kit, but small enough so as to not permit the components to pass through the opening. The opening may be covered with a transparent cover, such as plastic film.

In use, the user or patient uses the scoop device 10 accordingly to collect a fecal sample. The scoop device 10 including containing the fecal sample is placed in the container 30. The package 22 containing the luminol may be torn open at perforation 24 and poured into the container. To exhibit its luminescence, an amount of water (oxidant) sufficient to produce a mixture of the luminescent and sample is added. The lid may then be placed on the open end 36 of the container and the contents swirled, shaken, or otherwise sufficiently mixed to thoroughly mix the aqueous solution with the sample. The aqueous luminol mixture may be created in the container before the sample is added or vise versa. The order does not matter.

In one embodiment, the chemiluminescent compound undergoes a light-producing reaction which involves, as a reactant or catalyst, blood or blood components or products. In a more preferred embodiment, the chemiluminescent compound is luminol or a related compound, such as the examples listed above, which undergoes a luminescence-producing reaction in the container which is catalyzed by blood components, particularly the iron component of whole hemoglobin.

In the presence of iron, which is found in the hemoglobin of blood, and which functions as a catalyst, the luminol will luminesce. The container containing the sample is then viewed in darkened surroundings. The blood is therefore visible, or "glows" in the dark. The amount of luminol provided in the package 22 and water added to the container 30 should be sufficient to produce the result described in this application. The amount of luminol 20 and volume of water should be known by skilled artisans without undue experimentation.

The home test kit improves colorectal screening rates and saves lives as a result. The kit provides a private and convenient means for preliminarily detecting fecal blood. Upon detecting blood, individuals are more likely to consult a health care physician for a colorectal screening. The kit is formed from biodegradable material or material that easily disintegrates in water so that the kit may be toilet disposed without exposing individuals to infectious micro-organisms.

For the purposes of promoting an understanding of the principles of the invention, specific embodiments have been described. It should nevertheless be understood that the description is intended to be illustrative and not restrictive in character, and that no limitation of the scope of the invention is intended. Any alterations and further modifications in the described components, elements, processes, or devices, and any further applications of the principles of the invention as described herein, are contemplated as would normally occur to one skilled in the art to which the invention relates.

The invention claimed is:

1. A home test kit for detecting fecal blood comprising:
a scoop device for collecting a fecal sample;
a luminescent substance for mixing with the sample; and
a hollow substantially transparent container with an open end and a closed end formed from a biodegradable material that can dissolve or disintegrate in water for containing a mixture comprising the sample, the luminescent substance, and water,
wherein the mixture luminesces or glows as a result of iron present in hemoglobin such that blood in the sample is visually detectable by the human eye when the mixture is viewed in darkened surroundings.

2. The kit of claim 1, including a base with a cavity for receiving the closed end of the container so the container can be securely and releasably held in an upright attitude for viewing.

3. The kit of claim 1, including a lid connected to the container for closing the open end thereof.

4. The kit of claim 2, wherein the scoop, the container, and the base are formed from a biodegradable material.

5. The kit of claim 3, wherein the scoop, the container, the lid, and the base are formed from a material that can dissolve or disintegrate in water.

6. A home test kit for detecting fecal blood comprising:
a scoop device for collecting a fecal sample;
luminol for mixing with the sample; and
a substantially transparent hollow container with an open end and a closed end formed from a biodegradable material that can dissolve or disintegrate in water for containing a mixture comprising the sample, the luminol, and water,
wherein the mixture luminesces or glows as a result of iron present in hemoglobin such that blood in the sample is visually detectable by the human eye when the mixture is viewed in darkened surroundings.

7. The kit of claim 4, including a base with a cavity for receiving the closed end of the container so the container can be securely and releasably held in an upright attitude for viewing.

8. The kit of claim 6, including a lid connected to the container for closing the open end thereof.

* * * * *